United States Patent [19]

Razzano

[11] Patent Number: 5,420,325
[45] Date of Patent: May 30, 1995

[54] SILOXANE CRACKING PROCESS

[75] Inventor: John S. Razzano, Cohoes, N.Y.

[73] Assignee: General Electric Company, Waterford, N.Y.

[21] Appl. No.: 282,934

[22] Filed: Jul. 29, 1994

[51] Int. Cl.⁶ .................................. C07F 7/08
[52] U.S. Cl. ........................ 556/460; 556/461
[58] Field of Search .................... 556/468, 461

[56] References Cited

U.S. PATENT DOCUMENTS

| | | |
|---|---|---|
| 2,860,152 | 11/1958 | Fletcher . |
| 4,111,973 | 9/1978 | Bluestein . |
| 4,689,420 | 8/1987 | Baile et al. ............ 556/460 |
| 4,764,631 | 8/1988 | Halm et al. . |
| 5,241,097 | 8/1993 | Zupancic et al. ........ 556/460 |

Primary Examiner—Shaver, Sr. Paul F.

[57] ABSTRACT

The present invention relates to an improved cracking process for continuously making cyclic siloxanes.

14 Claims, No Drawings

SILOXANE CRACKING PROCESS

The present invention relates to a method of making cyclic siloxanes. More particularly it is concerned with the use of high boiling alcohol to make cyclic siloxanes from cracking reactions of silicone hydrolyzate.

BACKGROUND OF THE INVENTION

Organosiloxane polymers are prepared on an industrial scale using two basic processes. One is condensation which promotes the head to tail condensation of silanol terminated siloxane monomers or oligomers. The other one is equilibration which involves the catalytic rearrangement of siloxane bonds to form an equilibrated mixture. The term equilibration is used to describe the phenomenon which exists when the ratio of linear organosiloxane polymers to cyclic organosiloxane oligomers is maintained at a constant value. During the equilibration process, a constant breaking and forming of siloxane bonds takes place until the equilibrium point is reached. The massive breaking and forming of siloxane bonds permits the use of chainstoppers which will react to form a terminal non-chain extending group on the end of the polysiloxane molecule.

To produce useful silicone polymers by equilibration, the level of trifunctional units has to be very low, often less than 10 ppm. It is very difficult and expensive to produce low trifunctionality containing siloxanes except by a process known as "cracking". In the cracking process, a siloxane mixture containing more than 100 ppm trifunctionality is contacted with KOH at above 135° C. under vacuum to cause the siloxane mass to revert to cyclic siloxanes which distill from the reaction. Siloxanes, generally a hydrolyzate of silicone oil containing linear and cyclic species, are continuously fed to a reactor and are removed at the top of the reactor as cyclic siloxanes. It is well known that the trifunctional units react with the KOH to form a "potassium T salt" which is not volatile and cannot distill with cyclic siloxanes. In this way, trifunctionality is removed from the siloxanes and low trifunctional polymer can be made from cyclics produced by the cracking process. However, some of the trifunctional units remain in the siloxane hydrolyzate in the reactor and the concentration of this trifunctionality continues to increase with time during the cracking process. The buildup of trifunctionality substantially increases the viscosity of the siloxane hydrolyzate in the reactor. The solution becomes thicker and thicker until the reaction is forced to terminate because of the high viscosity. The higher the trifunctionality of the siloxane material fed to the reactor, the faster high viscosity is reached and the shorter the run length. In addition, as the viscosity increases during a run, the rate of "take off" of cyclics decreases, often by 30% or more during the course of the run. At the end of the run, the reactor mass contains so much trifunctionality that the mass is gelled or crosslinked. The reactor has to be shutdown frequently in order to take out the large, hard chunks of gels. These gels have no useful purpose and must be discarded, generally by placing it in a hazardous waster landfill.

U.S. Pat. No. 4,111,973 issued to Bluestein teaches an improved process for increasing the yield and purity of fluoroalkyl cyclotrisiloxanes in a cracking reaction of diorganopolysiloxanes by using, in addition to the cracking catalyst, an effective amount of a higher aliphatic alcohol as a stabilizing additive. This patent specifically directs to the method of making cyclotrisiloxanes. Fluoroalkylsiloxane has very low viscosity in the cracking reactor, thus the siloxane hydrolyzate in the reactor does not gel during the run. The alcohol is added to activate the catalyst rather than to reduce viscosity of the silicone hydrolyzate.

U.S. Pat. No. 4,764,631 issued to Halm et al. provides a method for preparing a product cyclopolydiorganosiloxane via the vapor phase rearrangement of other cyclopolydiorganosiloxanes or mixtures thereof. The vapor phase equilibration essentially eliminates the formation of gel.

U.S. Pat. No. 2,860,152 issued to Fletcher teaches a method of producing cyclic diorganosiloxanes having a composition different from the starting siloxane which comprises heating a mixture of the starting diorganosiloxane and an inert solvent boiling above 250° C. in amount of at least 20% by weight based upon the weight of the siloxane, in the presence of an alkaline catalyst under conditions of temperature and pressure insufficient to cause distillation of the solvent while simultaneously removing the desired cyclic diorganosiloxanes from the reaction zone. The inert solvent shifts the polymer/cyclic equilibrium of the reactor more to cyclics. The more cyclics in the reactor, the less tendency the reaction mass will gel. Fletcher requires at least 20% solvent to delay the gelation. The reaction slows down when too much solvent is put in the system. Further, when the reaction mass gels at the end of a run, the entire reaction content has to be disregarded since the siloxane/solvent cannot be separated from the gel. Thus Fletcher has not completely resolved the problem of gelation.

In none of the references, supra, is there any suggestion or demonstration of a process in which siloxane hydrolyzate containing high trifunctional units can be continuously cracked in the liquid phase without forming the gel.

Accordingly, there is a long-felt need to improve the efficiency of the process for producing cyclic siloxanes in commercial volume at the lowest possible cost.

There is also a need to maximize the yields and rate of formation of cyclic siloxanes from the cracking reaction of the silicone hydrolyzate.

Furthermore, in today's world with substantial ecological concerns it is necessary to eliminate the undesirable gel formed in the cracking process which must be disposed of in an environmentally affective manner.

SUMMARY OF THE INVENTION

In accordance with the above objects there is provided by the present invention an improved siloxane cracking process by adding an effective amount of high boiling alcohol to the liquid siloxane hydrolyzate. The high boiling alcohol causes the contents of the equilibration reactor to remain liquid and serves not only as a chainstopper but also as a solvent which shifts the polymer/cyclics equilibrium of the reactor more to cyclics. The use of high boiling alcohol allows the removal of trifunctional species in a highly efficient manner and completely eliminates formation of gel. The siloxanes and the alcohol in the residue can be recovered and reused.

DETAILED DESCRIPTION OF THE INVENTION

The present invention provides an efficient method to produce cyclic siloxanes of the formula, $$(R_2SiO)_x \tag{I}$$

where each R is independently selected from a group consisting of alkyl groups, alkenyl groups, aryl groups and alkaryl groups. x is an integral selected from 3 to 7.

The starting materials employed in the invention is a siloxane mixture containing linear and cyclic diorganosiloxane polymers. Such siloxane mixture is produced by the aqueous hydrolysis of dimethydichlorosilane containing more than 100 ppm of methyltrichlorosilane. The HCl produced in the hydrolysis process is removed from the silicone hydrolyzate and separately recycled.

The cracking reaction is carried out in the presence of a catalytic amount of cracking catalyst, preferably an alkali metal compound, more preferably, sodium hydroxide, potassium hydroxide, and cesium hydroxide. The most preferred catalyst is KOH.

The key feature of this invention is to add an effective amount of high boiling alcohol to prevent gelation and maintain high production rate of cyclics throughout the run. The preferred high boiling alcohols are those with boiling points above 300° C. so that they will stay in the reactor and will not distill over with the cyclic siloxanes, thus not contaminating the cyclic siloxanes in one aspect and in another aspect being present in the reactor so as to keep the reaction contents flowable. Most alcohols having a total carbon atom content of anywhere from 12–30 carbon atoms will operate in the present invention. The most preferred alcohol is stearyl alcohol which boiling point about 350° C. Alcohols with boiling points as low as 250° C. could be used, but require fractionation devices which will increase the investment cost of the cracking facility.

The level of the alcohol used in the reactor generally depends on the level of the trifunctional units in the siloxane hydrolyzate. The lower the level of the trifunctional units in the silicone hydrolyzate, the lower the level of the alcohol is required. At levels lower than 3% by weight of the silicone hydrolyzate, the alcohol functions primarily as a chainstopper. At levels higher than 3% by weight of silicone hydrolyzate, the alcohol is both a chainstopper and a processing aid to accommodate high trifunctionality levels (greater than 1000 ppm tri in di). The preferred concentration of the alcohol is in the neighborhood of 3% to 30% by weight of the silicone hydrolyzate. The level of the alcohol is more preferably between 6% to 25% by weight of the silicone hydrolyzate, and most preferably from 10% to 18%.

The method of this invention lends itself to either continuous or discontinuous operation. In a batch operation the alcohol, siloxane and catalyst are charged into a reactor and thereafter heated at the temperature and pressure necessary to cause the desired cyclic siloxanes to distill from the reactor. These conditions are maintained until all of the cyclic siloxane has been removed.

Alternatively the reaction may be carried out continuously. The stearyl alcohol is first charged to an empty reactor. The reactor is then sealed and the mixture of 45% KOH solution and siloxane hydrolyzate is continuously fed to the reactor. The KOH solution can be added into the reactor either after the hydrolyzate is added or can be co-fed with the hydrolyzate. It is well known that KOH reacts with the siloxane structure $MeSiO_{3/2}$ to produce a potassium "T" salt. While this "salt" is basic, it is not as strong as KOH for the cracking reaction, therefore, KOH is tied up by the $MeSiO_{3/2}$ as a potassium "T salt" occurs during the run. To maintain a constant level of KOH during the run, it is preferred to add KOH solution continuously throughout the run. The higher the trifunctional content is in the hydrolyzate, the higher the KOH is required. When the rate of takeoff is decreasing, the KOH addition rate should be increased.

During the startup, the silicone hydrolyzate containing more than 300 ppm may "gel" in the reactor. This is because the first reaction which takes place in the reactor is the condensation of the linear portion of the hydrolyzate to high polymer. In addition, the silanol terminated linears can form an "association" polymer with KOH which also increases the viscosity in the reactor. These reactions take place between 60° and 90° C. At these temperatures, KOH does not function as an equilibration catalyst, but is a very effective condensation catalyst. Therefore it is preferred to raise the temperature in the reactor to 130° C. as fast as possible. As the temperature of the reactor reaches 130° C., KOH starts to function as an equilibration catalyst. When this occurs, KOH equilibrates the alcohol to be the chainstopper, reducing the molecular weight of the polymer. The gel starts to break down as equilibration starts.

Temperature and pressure conditions in the reactor are controlled to alter the equilibrating mixture of linear and cyclics species to favor the formation of desired cyclic species. The preferred conditions for the cracking reaction are temperatures of above 140° C. and low pressure of 40 mm Hg or less. More preferred conditions are temperature in a range from about 140° to 165° C. and pressure in a range from about 10 to 40 mm Hg.

At this point the cyclic siloxanes formed in the cracking process can be separated by any known technique such distillation procedures. By simultaneously stripping off the cyclic siloxanes as they are formed, the yield of the cyclic siloxanes from the silicone hydrolyzate is maximized.

Since adding high boiling alcohol in the system can completely eliminate gelation, the reaction time is Substantially extended. The length of the run depends on the accumulation of potassium T salt. Generally the reaction is terminated when the potassium T salt is about 30–40% of the total content in the reactor. To begin the turnaround, the feed is shutoff and the reactor is "boiled down" until the takeoff rate is too low to be practical. As a result of this process; the level of the alcohol in the reactor increases by a factor of 2 or more. After the cracker is boiled down, it is cooled to about 90° C. This procedure reduces the content in the reactor and leaves room for water washing.

A large amount of water is added into the reactor to absorb the heat and prevent steam formation. Adding an equal volume of water to the reaction residual in the reactor gives a final temperature of about 68°–75° C., indicating a significant heat formation. With only a small amount of water addition, the reaction residual appears as a single phase. As more water is added, the reactor contents separate easily into two phases. It is critical to add at least one volume of water per volume of siloxane/alcohol in the reactor in order to achieve an excellent separation of the siloxane/alcohol layer and the aqueous layer.

After all the water is added, the agitator is shut off and the contents are allowed to settle for a certain period of time. The bottom aqueous phase has very high density because of the unreacted KOH and the "T"

salts, often a specific gravity of 1.24–1.30. The "organic layer" is not a single continuous phase. It generally consists of very fine "particles" of siloxane/alcohol suspended in an aqueous "matrix". Although the organic layer also contains "water", perhaps as much as 25–50%, the layer still separates easily from the bottom aqueous phase. During the whole process, it is preferred to keep the temperature of the reaction contents above the melting point of stearyl alcohol which is 56° C.

In the past, when the reaction is forced to terminate because of gelation, there is no effective method to separate the gel and the siloxanes in the residue. The siloxanes in the residue has to be disregarded. The instant invention can separate the "organic layer" which contains stearyl alcohol and residual siloxane hydrolyzate from the aqueous layer by any means known in the art. Both the siloxanes and the alcohol in the "organic layer" can be recycled for more than one run.

Without high boiling alcohol in the system, the residue at the end of the run time would be a hard gel which is difficult to remove from the reactor and clean the inner wall of the reactor. The instant process completely eliminates gelation in the cracking process. The residue at the end of each run is a very liquid-like organic phase. The inner wall of the reactor is clean and has no gel attached thereon. After removing the liquid residue, the reactor is immediately ready for the next run. The turnaround time is substantially shortened and the cost is substantially reduced.

The gel formed in the prior art processes has no useful purpose and must be landfilled. For a large commercial practice, the elimination of gel landfill cost saves hundreds of thousands of dollars. More importantly, the instant invention eliminates the undesirable hazardous waste and provide a major improvement for environment protection.

In the prior art process, the takeoff rate of the product cyclic siloxanes decrease when the viscosity of the reaction content builds up. By adding high boiling alcohol in the cracking process, the takeoff rate does not decrease during the course of the run. The run length can be substantially extended to weeks or months, depending on the trifunctionality level in the system. Thus the overall yields of the product cyclics siloxanes are substantially improved. The productivity depend on several factors such as the level of triorganosiloxane in the silicone hydrolyzate, the ratio of moles of triorganosiloxane to moles of the cracking catalyst, the alcohol level in the reactor, and etc.

Finally, it should be understood that the high boiling alcohols used in the instant process are not limited to stearyl alcohol, but may include any alcohol or amines that has a sufficiently high boiling point and is stable material at reaction conditions, which include high temperatures and high KOH levels. A mixture of two or more suitable alcohols can also be employed. The suitable high boiling alcohols can be, but not limited to the following:

| High Boiling Alcohol | Boiling Point (°F.) |
|---|---|
| $C_{12}H_{25}OH$ | 254° F. |
| $C_{14}H_{27}OH$ | 297° F. |
| $C_{16}H_{29}OH$ | 330° F. |
| $C_{18}H_{37}OH$ | 350° F. |

In order that those skilled in the art might be better able to practice the present invention, the following examples are given by way of illustration and not by way of limitation. All viscosities were measured at 25° C. Unless otherwise indicated, all parts are by weight.

EXAMPLE 1

A reactor was assembled with a stirrer, means for adding liquids to the reactor while the reactor was under vacuum, a vacuum line, a fractionating column with 7–8 theoretical plates and a condenser/collection vessel. 100 parts of a silicone hydrolyzate made by hydrolyzing dimethyldichlorosilane containing 1500 ppm methyltrichlorosilane as an impurity was added to the reactor along with 5 parts of a 45% aqueous solution of potassium hydroxide. The reactor was heated slowly to 150° C., and the vacuum was reduced and maintained at 30 torr. As the reactor was heated, a first cut of water with a small amount of cyclic siloxane was collected. The mixture was collected. The amount of cyclic siloxane was recovered. The water was discarded. At operating conditions of 150° C. and 30 torr, cyclics siloxanes were cracked in the reactor and collected in the receiver. The collection rate was 30 parts per hour. After the collection of 25 parts in the receiver, fresh hydrolyzate was added to the reactor under vacuum at a rate of 30 parts per hour. This allowed the reactor volume to remain constant during the reaction period. Aqueous KOH was added during the run at the rate of 0.2 parts of aqueous KOH per 100 parts of cyclic siloxanes removed by distillation.

The viscosity of the reactor content was low at the beginning of the run estimated at under 5000 cps. As hydrolyzate was fed to and product removed from the reactor, the viscosity of the reaction mass began to rise. After 300 parts of product was collected, the viscosity of the reactor contents had risen so high that large bubbles and foaming occurred. The agitator speed was increased to maintain product collection at 30 parts per hour. The viscosity continued to increase as the batch progressed. The foaming problem became worse and the bubbles became larger, forcing a reduction of takeoff rate throughout the last ⅔ of the run. Towards the end of the run, the takeoff rate was about 15 parts per hour. As the takeoff rate reduced, the amount of hydrolyzate and 45% aqueous KOH fed to the reactor was correspondingly decreased. After 4800 parts of product had been collected, the reactor viscosity was so high that the agitator had almost stalled. Addition Of hydrolyzate and KOH was discontinued, and the reactor was boiled down to recover as much product as possible. The reactor contents gelled and the process was forced to terminate. Water was added to the reactor when it was cooled to 95° C. to facilitate easy removal of the gel, as the water allowed the gelled mass to break into small to medium size chunks. The inner wall of the reactor was coated with a heavy gel which had to be removed forcefully in order to have efficient heat transfer surface during the next batch. The amount of gel collected and discarded was 25 parts.

EXAMPLE 2

The setup was the same as in Example 1. The reactor was charged with 100 parts of the same hydrolyzate as in Example 1, and 5 parts of 45% aqueous KOH. In addition 15 parts of stearyl alcohol was also added into the reactor. The process was started up and run exactly as in Example 1, with 30 parts an hour of takeoff. The viscosity of the batch did not noticeably increase. The takeoff rate could be maintained 30 parts/hr throughout the entire run. The total takeoff of product was 13300 parts. At the end of the run, the viscosity was still low and no gel was apparent. The reactor was boiled down so that 60 parts of the reaction content were left in the reactor. The reactor was cooled to 90° C. 80 parts of water was added into the reactor and agitated. The agitator was stopped and the reactor contents separated into two phases. The bottom aqueous phase had a specific gravity of 1.20, representing soluble salts including potassium "T" silanolate and unreacted KOH. The aqueous layer was discarded and 50 parts more water was added into the reactor and agitated. The second aqueous layer was discarded after a clean separation.

The run is about twice as long as that in Example 1. No gel was formed and no siloxanes had to be discarded. In addition, the inner wall of the reactor was clean and can be used for the next run immediately.

To start a next run, 50 parts of the same hydrolyzate and 5 parts of 45% aqueous KOH were added to the reactor residues from the first run. 45% aqueous KOH was added at 0.2% parts per hour. Viscosity remained low during the entire run and takeoff was maintained at 30 parts per hour until 10000 parts were collected as product. The reactor was boiled down to 50 parts and the contents were washed twice with water exactly as previously. Again, no gel was found in the reactor and no siloxanes needed to be discarded. The inner wall of the reactor had no gel.

The entire procedure of startup, feeding and takeoff at a 30 parts per hour was performed a third time with no noticeable viscosity built. The run continued until 10,000 parts of product were collected. The batch was water washed exactly as previously. There was no gel in the residue and no siloxanes were discarded.

|  | Ex. 1 | Ex. 2, Run 1 | Ex. 2, Run 2 |
|---|---|---|---|
| FEED (PARTS) | | | |
| Oil | 100 | 100 | 50+ residual siloxane hydrolyzate from Ex. 2, Run 1 |
| 45% KOH | 5 | 5 | 5 |
| Stearyl Alcohol | 0 | 15 | 15 |
| OUT (PARTS) | | | |
| Cyclic Siloxanes | 4,800 | 13,000 | 10,000 |
| RUN LENGTH (DAYS) | 7 | 13.3 | 10.2 |
| RESIDUE PROPERTIES | Hard gel | no gel viscosity less than 10,000 cps | no gel viscosity less than 10,000 cps |
| AVERAGE TAKEOFF | 1.0 | 1.3 | 1.3 |
| AVERAGE YIELD (%) | 99 | 100 | 100 |
| UPTIME | 85% | 90% | 88% |
| Production / (Production + Turnaround) | | | |
| OVERALL RELATIVE EFFICIENCY | 1.0 | 1.5 | 1.4 |

Many variations of the present invention will suggest themselves to those of ordinary skill in the art in light of the above-detailed description. All such obvious modifications are within the full intended scope of the appended claims.

What is claimed is:

1. A process for making cyclic siloxanes, comprising the steps of
   (a) mixing siloxane hydrolyzate containing trifunctional units with a catalytic amount of catalyst;
   (b) adding an effective amount of high boiling alcohol to the mixture of said step (a);
   (c) controlling reaction conditions to favor formation of the cyclic siloxanes; and
   (d) simultaneously recovering the cyclic siloxanes whereby the alcohol substantially reduces the viscosity of the siloxane hydrolyzate.

2. The process of claim 1, wherein the cracking catalyst is an alkali metal compound.

3. The process of claim 2, wherein the alkali metal compound is selected from a group consisting of sodium hydroxide, potassium hydroxide, cesium hydroxide and mixtures thereof.

4. The process of claim 1, wherein the boiling point of the alcohol is above 250° C.

5. The process of claim 4, wherein the boiling point of the alcohol is above 300° C.

6. The process of claim 1, wherein the alcohol is selected from a group consisting of straight chain aliphatic alcohols and amines, branched aliphatic alcohols, arylalkylalcohols and mixtures thereof.

7. The process of claim 6, wherein the alcohol is stearyl alcohol.

8. The process of claim 7, wherein the stearyl alcohol is added to the silicone hydrolyzate at a concentration of at least 3%.

9. The process of claim 8, wherein the stearyl alcohol is added to the silicone hydrolyzate at a concentration of 10%.

10. The process of claim 9, wherein the stearyl alcohol is added to the silicone hydrolyzate at a concentration of 18%.

11. The process of claim 1, wherein said step (c) further comprises the step of heating the reaction mixture to 140° to 165° C. at a vacuum of 10 to 40 mm Hg.

12. The process of claim 1, wherein the product cyclic siloxanes are recovered by distillation.

13. The process of claim 1, further comprises the steps of
   (e) adding a sufficient amount of water to the reaction mixture; and
   (f) recovering the siloxanes and the alcohol in the reaction mixture.

14. The process of claim 13, wherein the volume of the water added is at least equal to the volume of siloxanes and alcohol in the reaction mixture.

* * * * *